United States Patent
Morshed et al.

(10) Patent No.: US 12,369,831 B1
(45) Date of Patent: Jul. 29, 2025

(54) APPARATUS AND METHOD TO CAPTURE BODY SIGNALS WITH CONJUGATE COILS AND PAIRED COILS

(71) Applicants: Bashir I. Morshed, Germantown, TN (US); Mohammad Abu-Saude, Sunnyvale, CA (US)

(72) Inventors: Bashir I. Morshed, Germantown, TN (US); Mohammad Abu-Saude, Sunnyvale, CA (US)

(*) Notice: Subject to any disclaimer, the term of this patent is extended or adjusted under 35 U.S.C. 154(b) by 923 days.

(21) Appl. No.: 16/396,701

(22) Filed: Apr. 28, 2019

Related U.S. Application Data

(60) Provisional application No. 62/664,329, filed on Apr. 30, 2018.

(51) Int. Cl.
| | |
|---|---|
| *H01Q 1/00* | (2006.01) |
| *A61B 5/00* | (2006.01) |
| *A61B 5/30* | (2021.01) |
| *A61B 5/302* | (2021.01) |
| *A61B 5/25* | (2021.01) |
| *A61B 5/316* | (2021.01) |

(52) U.S. Cl.
CPC ............ *A61B 5/302* (2021.01); *A61B 5/0006* (2013.01); *A61B 5/30* (2021.01); *A61B 5/0015* (2013.01); *A61B 5/0031* (2013.01); *A61B 5/25* (2021.01); *A61B 5/316* (2021.01); *A61B 5/6801* (2013.01); *A61B 2562/0214* (2013.01)

(58) Field of Classification Search
CPC ......... A61B 5/302; A61B 5/30; A61B 5/0006; A61B 5/0015; A61B 5/0476
See application file for complete search history.

(56) References Cited

U.S. PATENT DOCUMENTS

| | | | |
|---|---|---|---|
| 5,217,010 | A | 6/1993 | Tsitlik |
| 5,392,784 | A | 2/1995 | Gudaitis |
| 5,458,123 | A | 10/1995 | Unger |
| 9,853,611 | B2 | 12/2017 | Chang et al. |
| 10,405,746 | B2 | 9/2019 | Morshed et al. |
| 10,973,430 | B2 | 4/2021 | Morshed et al. |
| 2002/0067269 | A1 | 6/2002 | Cadell et al. |
| 2005/0203366 | A1 | 9/2005 | Donoghue et al. |
| 2006/0009817 | A1 | 1/2006 | Tulkki |
| 2006/0066449 | A1 | 3/2006 | Johnson |
| 2007/0247316 | A1 | 10/2007 | Wildman |
| 2008/0119716 | A1 | 5/2008 | Boric-Lubecke et al. |

(Continued)

FOREIGN PATENT DOCUMENTS

DE 19904033252 * 4/1992 ............... G01D 5/22

*Primary Examiner* — Joseph J Lauture
(74) *Attorney, Agent, or Firm* — Wayne Edward Ramage; Baker Donelson

(57) ABSTRACT

A wireless resistive analog passive (WRAP) sensor system using inductive coupling between two or more planar printed spiral coils (PSCs) configured to capture various physiological signals, such as, but not limited to, heart rate, respiration rate, pulse oxymeter, and core body temperature. The sensor system particularly useful for capturing physiological signals that require differential inputs, such as an ECG, EKG, EMG or EEG signals. Wireless induction coupling signals are transmitted over longer range using a fully-passive (i.e., battery-less) range extender circuit comprising a paired coil. The sensor system may include body-worn, fully-passive (battery-less) sensors.

11 Claims, 8 Drawing Sheets

(56) References Cited

U.S. PATENT DOCUMENTS

| | | |
|---|---|---|
| 2008/0159365 A1 | 7/2008 | Dubocanin et al. |
| 2008/0241077 A1 | 10/2008 | Eickmeier et al. |
| 2010/0106041 A1 | 4/2010 | Ghovanloo et al. |
| 2011/0004276 A1 | 1/2011 | Blair et al. |
| 2011/0112382 A1* | 5/2011 | Li ............... A61B 5/02427 600/301 |
| 2011/0251469 A1 | 10/2011 | Varadan |
| 2012/0095361 A1 | 4/2012 | Xu et al. |
| 2012/0146795 A1 | 6/2012 | Margon et al. |
| 2012/0242501 A1 | 9/2012 | Tran |
| 2013/0231947 A1 | 9/2013 | Shusterman |
| 2013/0338518 A1 | 12/2013 | Zoica |
| 2014/0051946 A1 | 2/2014 | Arne et al. |
| 2014/0107501 A1 | 4/2014 | Komanduri et al. |
| 2014/0194944 A1 | 7/2014 | Romanelli et al. |
| 2014/0371611 A1 | 12/2014 | Kim |
| 2015/0289763 A1* | 10/2015 | Morshed ............ A61B 5/0015 340/870.07 |
| 2016/0113540 A1 | 4/2016 | Chi |

\* cited by examiner

APPARATUS AND METHOD TO CAPTURE BODY SIGNALS WITH CONJUGATE COILS AND PAIRED COILS

This application claims benefit of and priority to U.S. Provisional Application No. 62/664,329, filed by Bashir I. Morshed, et al., on Apr. 30, 2018, which is incorporated herein in its entirely by specific reference for all purposes.

FIELD OF THE INVENTION

The present invention relates generally to systems and methods for capturing physiological and neurological signals from a subject. More specifically, the invention relates to wireless resistive analog passive (WRAP) sensors with conjugate coils and paired coils for measuring differential and other types of neurophysical signals.

BACKGROUND OF THE INVENTION

The assessment of bioelectric potentials or biophysical signals generated by the body is a commonly used method of monitoring health status. Such systems, like the electrocardiogram (ECG or EKG), provide a noninvasive, painless test with rapid results and are standard equipment in the medical and veterinary communities. However, sensors typically employed by such devices are often obtrusive and may require external power sources or batteries. Furthermore, wired sensing devices are cumbersome for the wearer and are at risk of being damaged or misaligned during use, particularly if the associated wires become entangled with clotting or are otherwise disturbed by the wearer's movements. These issues are further confounded when the sensing device is implanted or must be worn for longer periods of time.

Wireless sensors are useful when a wired connection is inconvenient or impractical, such as with body-worn sensors, implantable sensors, and remote sensors. In addition, passive wireless sensors can eliminate contact wires and batteries, making continuous patient monitoring in day-to-day life more practical. Current wireless passive sensors require the use of a digital chip, which significantly increases the cost of the devices and can often lead to failure of the device.

Current wireless analog passive (WRAP) sensors are not able to receive physiological signals where information is contained in differential inputs, such as ECG, EMG and EEG signals. In the case of wired counterparts, differential amplifiers are employed to address this issue. These amplifiers reject most of the common mode noise while simultaneously amplifying differences between the two signals. The related metric is commonly known as Common Mode Rejection Ratio (CMMR). As differential amplifiers require a power supply, they cannot be employed in passive (e.g., WRAP) sensors, which are batteryless. In addition, the maximum range of coupling in current passive (e.g., WRAP) sensors is very small (less than 10 cm), which limits the distance between the sensor coil and the scanner coil.

Examples of prior art bio-sensor systems are disclosed in Morshed, U.S. Pub. No. 20170135215 (U.S. Pat. No. 10,182,499, issued Jan. 15, 2019) ("Multilayer Additive Printed Circuit"); and Morshed, et al., U.S. Pub. No. 20160128596 (U.S. application Ser. No. 14/938,954) ("Fully Reconfigurable Modular Body-Worn Sensors"); all of which are incorporated herein by specific reference in their entireties for all purposes. Further details about the operation of WRAP sensors, and the wireless passive sensing of physiological and biopotential sensing using WRAP sensors, are disclosed in Morshed, et al., U.S. Pub. No. 20150289763 (U.S. application Ser. No. 14/686,275) ("Wireless Analog Passive Sensors"), which is incorporated herein by specific reference in its entirety for all purposes.

Accordingly there is a need for accessing differential inputs from more than one electrodes of WRAP sensors, which are unobtrusive, wireless, and passive body-worn sensors to collect physiological signals. There is a further need for a system and method for extending the range of WRAP sensing devices such that the sensor and interrogator can be placed further apart on the body.

SUMMARY OF THE INVENTION

In various exemplary embodiments, the present invention comprises wireless resistive analog passive (WRAP) sensors that can transmit analog signals without any digital chips. Embodiments of the novel WRAP sensors use inductive coupling between two or more printed spiral coils (PSCs) and are configured to capture various physiological signals, such as, but not limited to, heart rate, respiration rate, pulse oxymeter, and core body temperature. The present invention is particularly useful for capturing physiological signals that require differential inputs, such as an ECG, EMG or EEG signal.

The invention further comprises systems and methods to allow differential signals (such as EKG/ECG, EMG, EEG, and the like) to be captured using wireless induction coupling using a conjugate coil pair. In certain embodiments, the invention comprises systems and methods for transmitting wireless induction coupling signals over longer range using a fully-passive (i.e., battery-less) range extender circuit comprising a paired coil. The range extender can be used not only for the disclosed ECG WRAP sensor, but also previously disclosed WRAP sensors, including heart rate, respiration rate, pulse oxymeter, and core body temperature sensors. In one embodiment, the present invention comprises body-worn, fully-passive (battery-less) sensors.

DETAILED DESCRIPTION OF EXEMPLARY EMBODIMENTS

Figure 1:
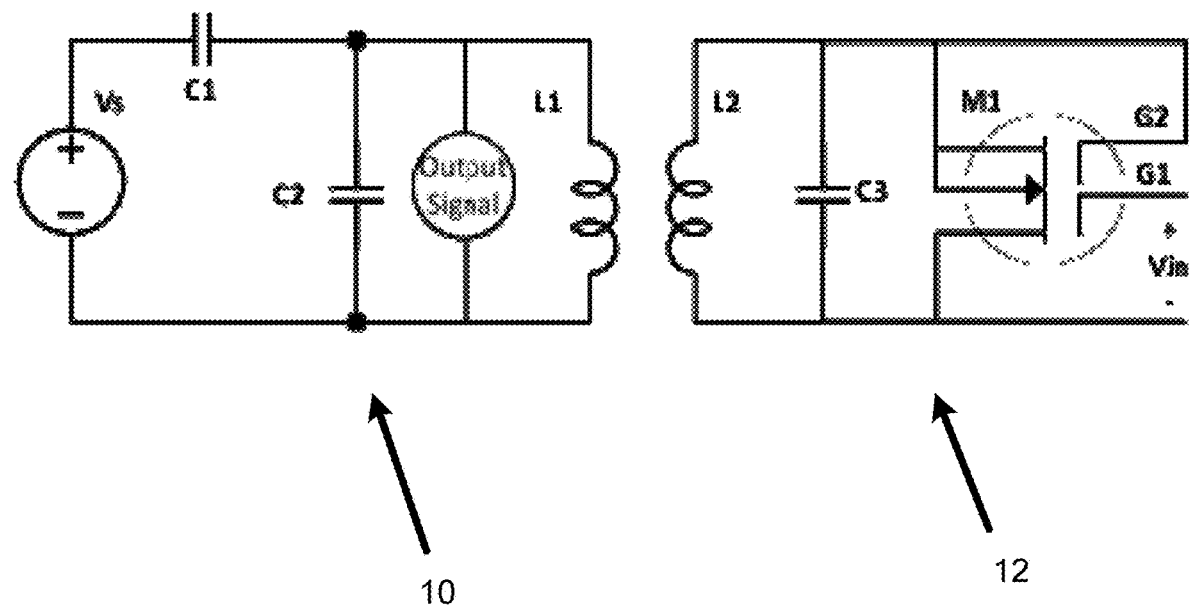
FIG. 1 provides a diagram of a fully-passive, simplified system with scanner (L1) and sensor (L2) coils for single channel bio-potential sensing using the WRAP system.

All patents, patent applications, and publications cited herein are hereby incorporated by reference in their entirety. The disclosures of these publications in their entireties are hereby incorporated by reference into this application in order to more fully describe the state of the art as known to those skilled therein as of the date of the invention described and claimed herein.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

Detailed descriptions of one or more preferred embodiments are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in any appropriate manner.

The singular forms "a," "an" and "the" include plural reference unless the context clearly dictates otherwise. The use of the word "a" or "an" when used in conjunction with the term "comprising" in the claims and/or the specification may mean "one," but it is also consistent with the meaning of "one or more," "at least one," and "one or more than one."

Wherever any of the phrases "for example," "such as," "including" and the like are used herein, the phrase "and without limitation" is understood to follow unless explicitly stated otherwise. Similarly "an example," "exemplary" and the like are understood to be nonlimiting.

The term "substantially" allows for deviations from the descriptor that do not negatively impact the intended purpose. Descriptive terms are understood to be modified by the term "substantially" even if the word "substantially" is not explicitly recited. Therefore, for example, the phrase "wherein the lever extends vertically" means "wherein the lever extends substantially vertically" so long as a precise vertical arrangement is not necessary for the lever to perform its function The terms "comprising" and "including" and "having" and "involving" (and similarly "comprises," "includes," "has," and "involves") and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a process involving steps a, b, and c" means that the process includes at least steps a, b and c. Wherever the terms "a" or "an" are used, "one or more" is understood, unless such interpretation is nonsensical in context.

As used herein the term "about" is used herein to mean approximately, roughly, around, or "in the region of." When the term "about" is used in conjunction with a numerical range, it modifies that range by extending the boundaries above and below the numerical values set forth. In general, the term "about" is used herein to modify a numerical value above and below the stated value by a variance of 20 percent up or down (higher or lower).

The WRAP ECG system disclosed herein comprises a pair of conjugate coils that are in mirror opposite configuration. When so situated, the induced magnetic field by two coils cancels each other when signals are common (common mode signal), but do not cancel when signals are different (differential mode signal). This allows differential mode signals such as ECG to be captured with the WRAP sensor technique.

Under several exemplary embodiments, the invention comprises a novel WRAP sensor for measuring differential ECG signals using one primary coil and a pair of secondary conjugate coils. The differential inputs are connected to two simple amplifiers such as metal-oxide-semiconductor field-effect transistors (MOSFETs) that change loading of the two secondary coils. As a result, the common signal of both sensor coils are cancelled out while differential signals are transmitted, and leads to the ability to access only differential bio-potential signals that modulate the carrier signal at the primary.

FIG. 1 shows a simplified schematic of a scanner 10 and sensor 12 components for a system for bio-potential sensing using a single loop antenna (i.e., coil) (L1) in the scanner and a single loop antenna (i.e., coil) (L2) in the sensor.

Figure 2:
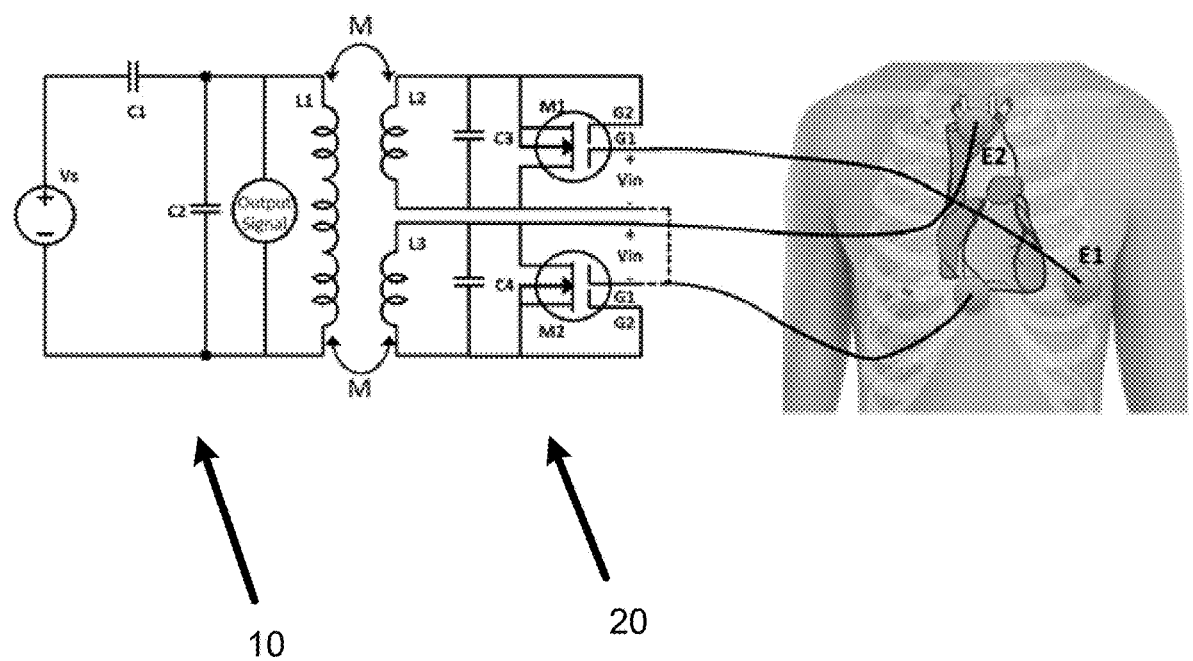
FIG. 2 shows a diagrammatic representation of an exemplary WRAP ECG system that employs a scanner coil (L1) and a sensor conjugate coil pair (L2-L3) for bio-potential sensing. The WRAP ECG sensors are shown connected to a series of electrodes attached to the chest area of a human subject.

FIG. 2 shows an exemplary of a WRAP ECG sensor for bio-potential signal access using a conjugate coil pair (L2, L3) in the sensor component 20. This embodiment is configured to sense the differential input voltages between electrodes E1 and E2. Three spiral coils are shown. Two identical coils (L2 and L3) are presented in conjugate orientation as passive sensors in the sensor component 20 and one coil (L1) as a scanner device 10. When so oriented, the magnetic field of conjugate coil (L2) opposes the other (L3), and vice versa. Certain embodiments employ a dual gate depletion mode MOSFET for bio-potential capture due to its high sensitivity for small input voltages (Vin). In the FIG. 2 embodiment, input voltage is converted to a correlated resistive variation of source-drain resistance of the MOSFET ($R_{SD}$: resistance between Source and Drain terminals).

Figure 3A:
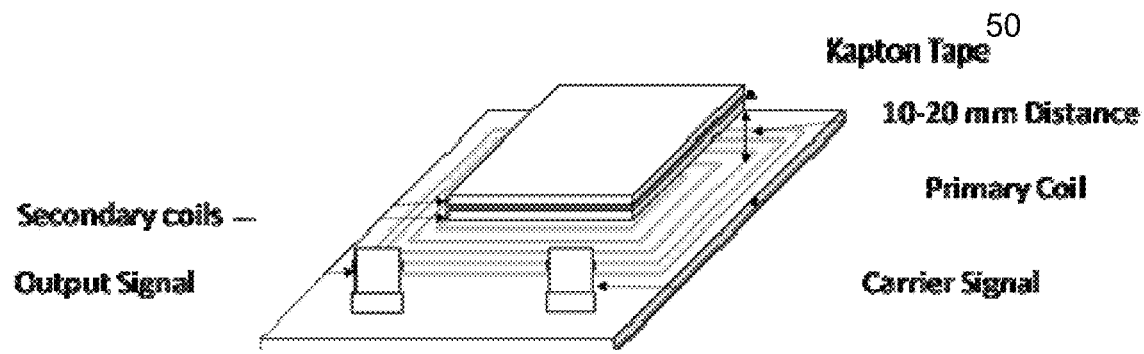
FIG. 3A provides a top perspective schematic view of an exemplary WRAP ECG sensor system with a scanner coil (primary) and a sensor conjugate coil pair (secondary) positioned at a co-axial position.
Figure 3B:
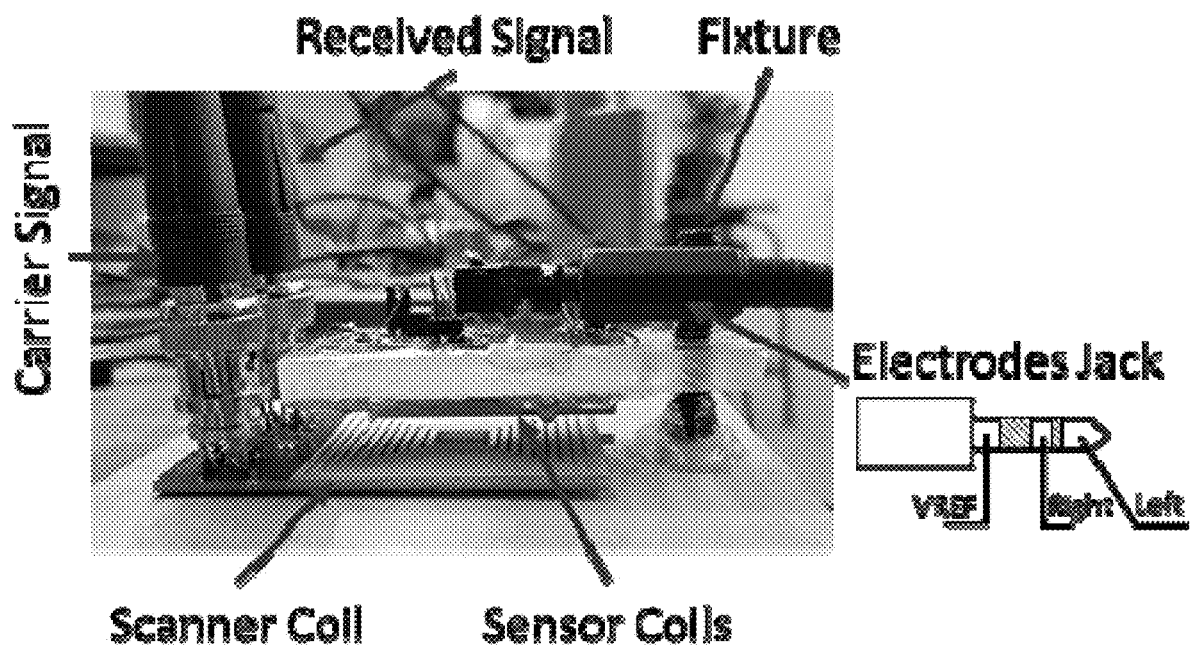
FIG. 3B is a photographic view of an exemplary WRAP ECG sensor system with a scanner coil (primary) and a sensor conjugate coil pair (secondary) positioned at a co-axial position.

The primary printed circuit board (PCB) comprises two subminiature version A ("SMA") coaxial RF connectors (see FIG. 3B), one for the carrier input that oscillates at an RF carrier wave (8.37 MHz used in this embodiment), and the other one is across the coil L1 and carries the modulated signal to another printed circuit board with electronic circuits for detecting, filtering, and amplification. The capacitor C1 is used to match the antenna to 50Ω and capacitor C2 is used to adjust the resonance frequency with L1. The loop antennas (L1, L2, and L3) are designed as planar printed spiral coils (PSC) and can be modeled as inductors. The passive sensors have identical circuits where C3 and C4 are used to tune the antenna at the resonance frequency. The Gate-1 (G1) of one MOSFET and drain of that MOSFET are connected to one set of the electrodes (i.e. one channel), while the Gate-1 (G1) of the other MOSFET and drain of that MOSFET are connected inversely to the other set of electrodes (i.e. second channel) to collect the difference of the two signals (e.g. two channels on the body to capture ECG signal) by combining one of the G1 to the other drain as a single reference electrode. The second gates, Gate-2 (G2), are connected to source of corresponding MOSFET to increase sensitivity for $V_{in}$ sensing (μV-range).

In one embodiment, the outer diameter of the primary and the secondary coils are 40 and 20 mm, respectively. The planar coils of the sensor boards can be placed to face each other with an isolation material between the two coils (shown in FIG. 3A). In one embodiment, the insulation material comprises a polyimide film, such as Kapton® tape 50 (manufactured by E.I. du Pont de Nemours and Company, Wilmington, Del., USA). The planar coils and the insulation material can be also printed between the traces, such as disclosed in "Multilayer Additive Printed Circuit", U.S. Pat. No. 10,182,499 (referenced above and incorporated herein by specific reference for all purposes). A fixture can be employed to maintain the boards in parallel at a co-axial position. In other embodiments, the conjugate PSCs can be within the same circuit board printed on different layers or on different sides. In other embodiments, the conjugate coils can be designed to occupy the same layer or same side by employing a double spiral design of a single PSC.

Figures 4A, 4B, 4C:
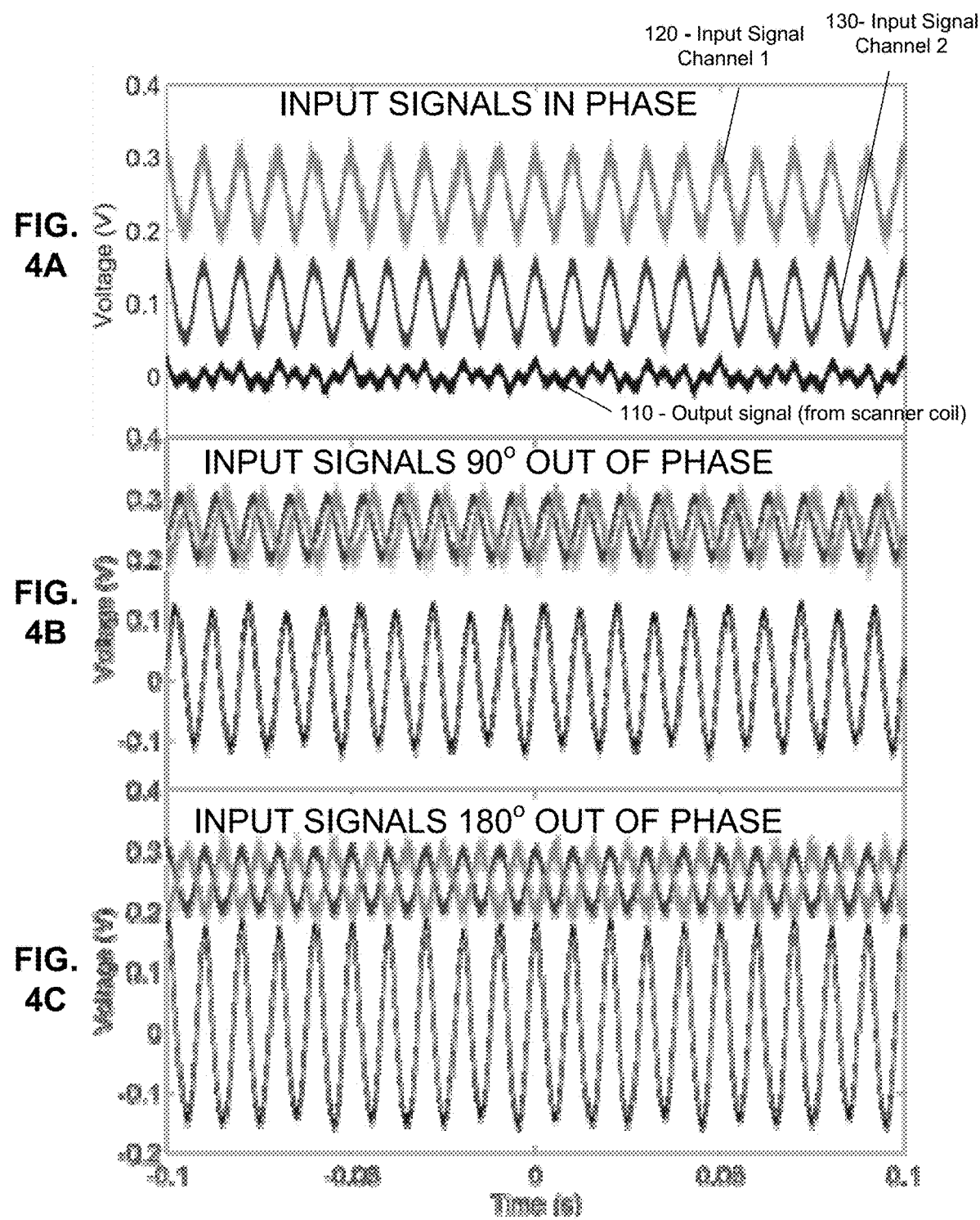
FIGS. 4A-C show graphical representations of sinusoidal signal waves (inputs 1 and 2 from sensor conjugate coil pair, first two waveforms, output from scanner coil, the last waveform) captured using an exemplary conjugate coil pair WRAP system with input signals in phase (4A), 90° out of phase (4B), and 180° out of phase (4C).

FIGS. 4A-C provide a graphical representation of experimental signals captured using a conjugate coil pair as discussed above. These data employed the differential passive sensor setup (two sensors with a conjugate coil pair) to show the responses to differential mode and common mode input voltages. In FIGS. 4A-4C, the received signal 110 (third waveform, blue) is the difference between Vin1 120 (first waveform, green) and Vin2 130 (second waveform, red). The input signals of FIG. 4A are shown with difference between phase equal to 0° (in phase); the input signals of FIG. 4B are shown at 90° (out of phase); and the input signals of FIG. 4C are shown at 180° (anti-phase). Both Vin1 and Vin2 are sinusoidal signals with a peak-to-peak voltage of 100 mV and frequency of 100 Hz. The results show that the output signal is significantly attenuated when both input signals are identical (FIG. 4A), while the output signal is amplified when they have maximum difference (FIG. 4C).

Figure 5A:
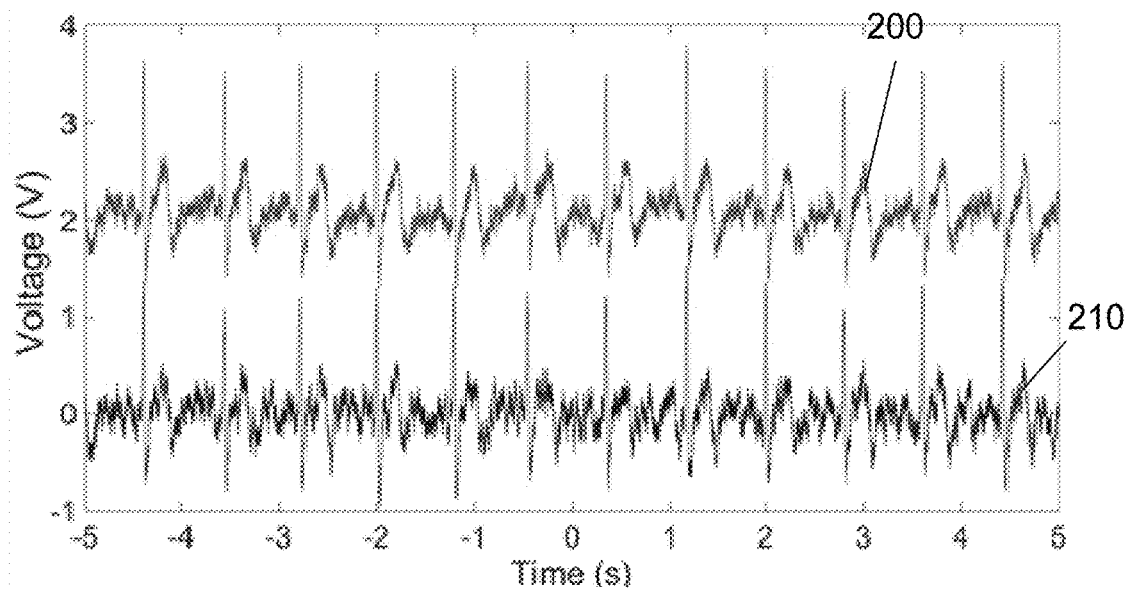
FIG. 5A shows a comparison of an ECG signal captured with an off-the-shelf, commercially available ECG device (top) to an ECG signal captured using an exemplary WRAP ECG sensor with conjugate coils (bottom).

FIG. 5A shows a comparison of ECG obtained signals from commercial ECG hardware (in this case, manufactured by OLIMEX EKG/EMG shield; Olimex, Ltd, Plovdiv, Bulgaria) to those obtained from the presently-disclosed conjugate coil pair WRAP ECG system. In vivo ECG data was captured using commercial gel type ECG electrodes Ag/AgCl (GS-26, Pre-gelled Disposable sEMG Electrodes, Multi BioSensors Inc.).

Figure 5B:
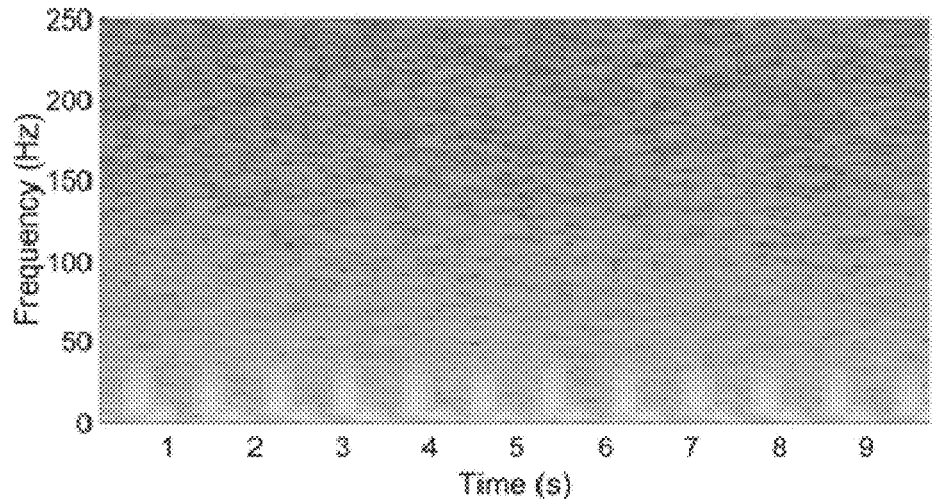
FIGS. 5B and 5C shows time frequency domain comparison of an ECG signal captured using the commercially available ECG device (5B) with the exemplary WRAP ECG system (5C).
Figure 5C:
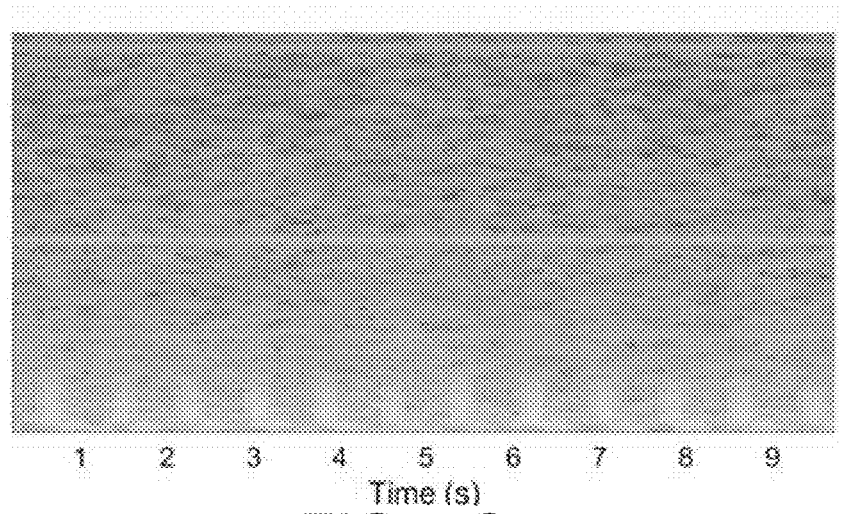
Figure 6:
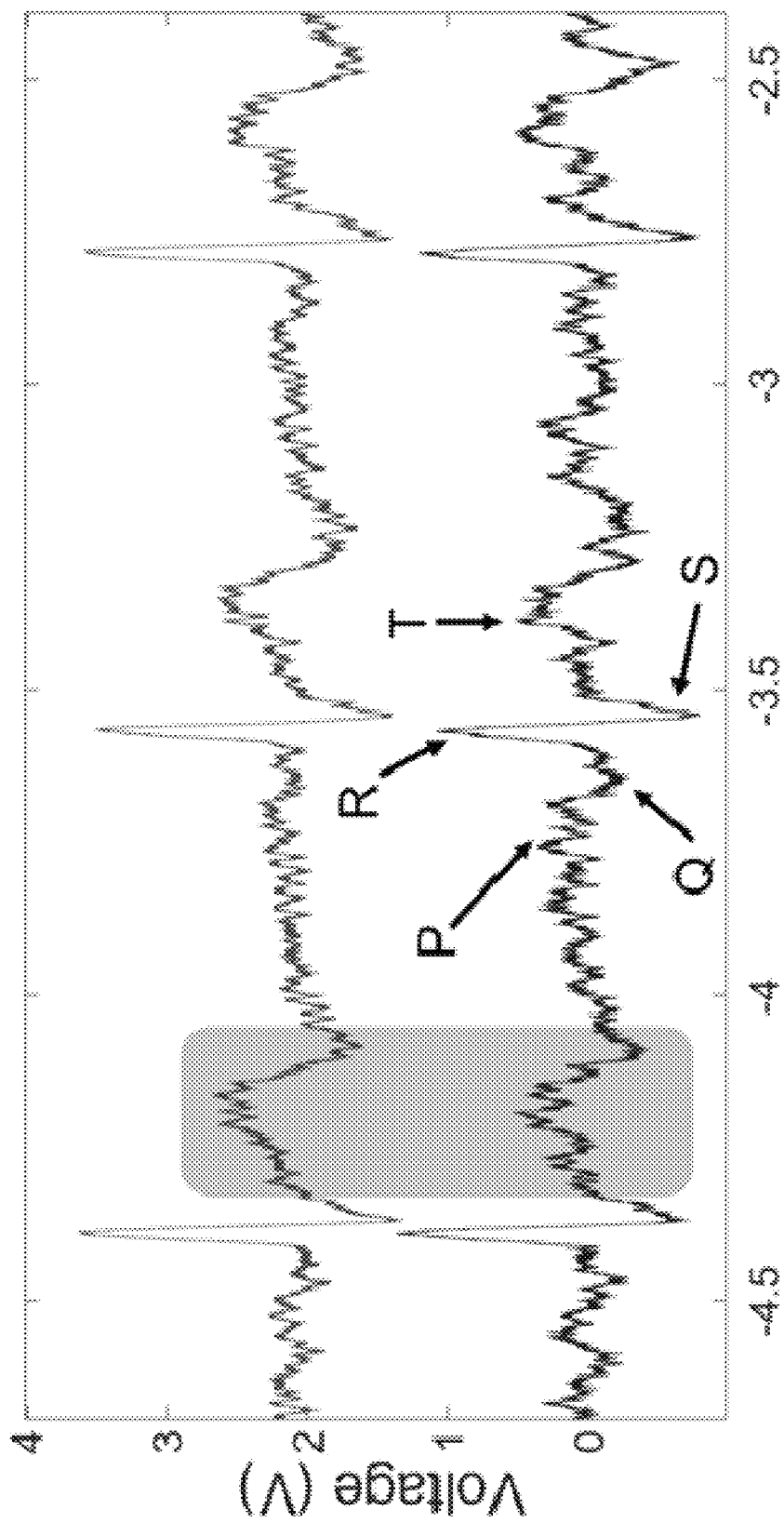
FIG. 6 is a graphical chart comparing the ECG signals collected from the commercially available ECG device (top) and those collected using the exemplary WRAP ECG system (bottom). The PQRST signals are identified on the signal obtained from the WRAP ECG sensor with a conjugate coil pair.

FIG. 5A shows the raw data of the ECG signal recorded using the commercial ECG device (top waveform, red 200) and the passive sensor (bottom waveform, blue 210). Some noise can be seen in the unprocessed signal using time-frequency analysis of the passive sensor data, which can be de-noised using an analog or a digital filter. FIG. 5B shows the time-frequency analysis of the ECG signals obtained from the commercial device, and FIG. 5C shows the time-frequency analysis of the ECG signals obtained from an embodiment of the presently disclosed passive sensor. These data reveal that the ECG signals recorded using the presently disclosed passive sensor (FIG. 5C) had more components of the utility line (e.g., 60 Hz) noise and its harmonics than the data from the commercial device (FIG. 5B). However, as seen in FIG. 6, all of the ECG components (R-peaks, QRS-complexes, T-waves, and P-waves) are easily recognizable from the raw data without any downstream processing.

Figure 7:
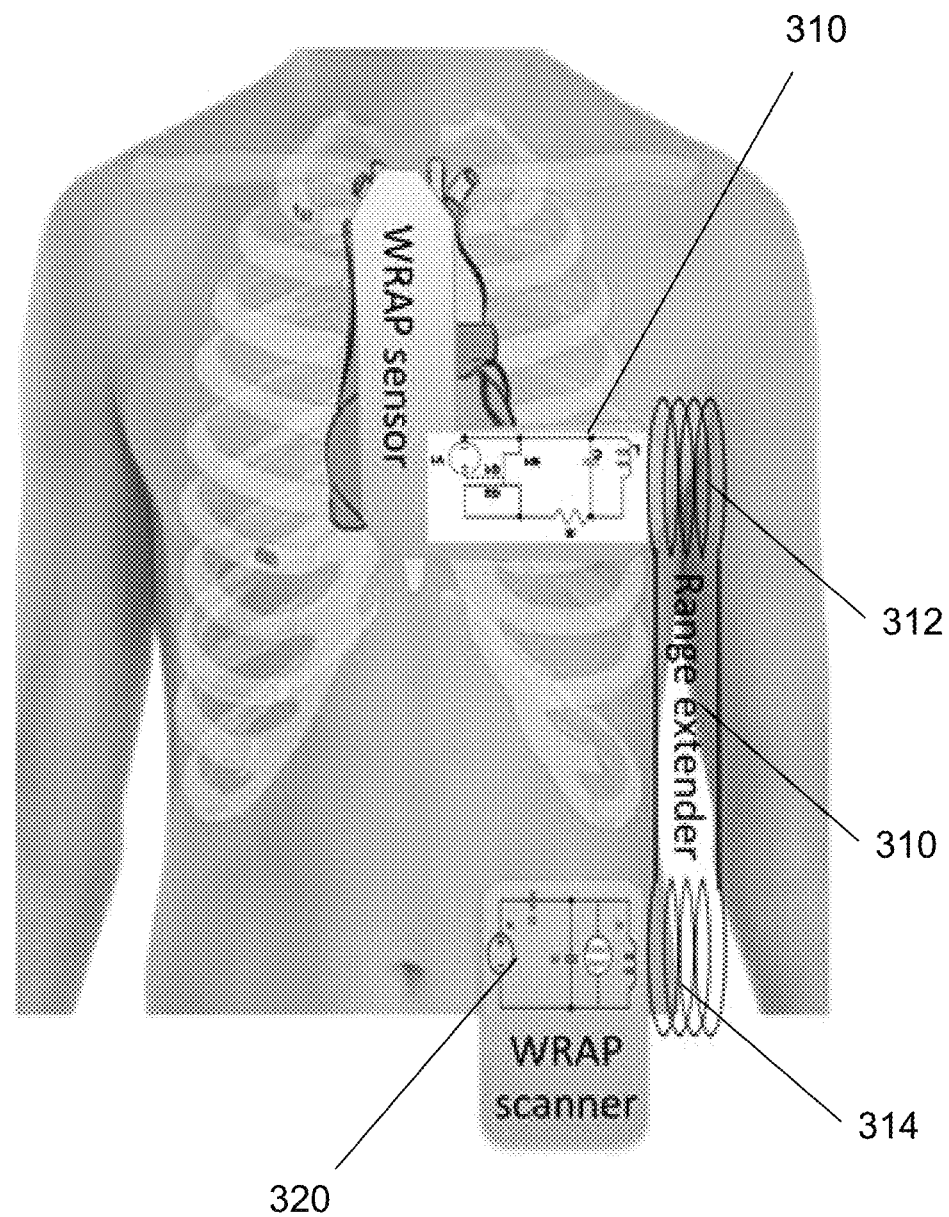
FIG. 7 provides a schematic view of an exemplary WRAP system employing a range extender with a paired coil between the sensor and the scanner components.

FIG. 7 provides a schematic representation of a range extender 300 comprising a paired coil connecting a WRAP passive sensor 310 to a WRAP scanner 320, in accordance with an exemplary embodiment of the present invention. This arrangement permits the scanner coil to be physically separated far from the sensor coil via a fully-passive paired coil circuit (battery-less), while still permitting power and data collection. In several embodiments, the range extenders comprise at least two coils 312 314. In FIG. 7, a first coil 314 of the range extender is coaxially positioned adjacent to the WRAP scanner coil, and a second coil 312 of the range extender is adjacent to the WRAP sensor (e.g., WRAP ECG sensor), permitting the scanner and sensor to be communicatively linked over a given distance. The paired coils are connected using flexible wires, and optionally can have tuning capacitors connected in parallel to coils for resonant coupling.

As can been seen, the number of coils employed by the range extender will vary with the number of sensors, scanners, or both. The range extender can be easily releasably attached to the user's body or to the user's clothing (such as undergarments). In several embodiments, the range extender is embedded, woven, or stitched within clothing worn by the user. The range extender thus, for example, allows the sensor to be attached to the user's chest, while the scanner is attached to the waist (e.g., on a belt, in a pocket, or the like).

Figure 8:
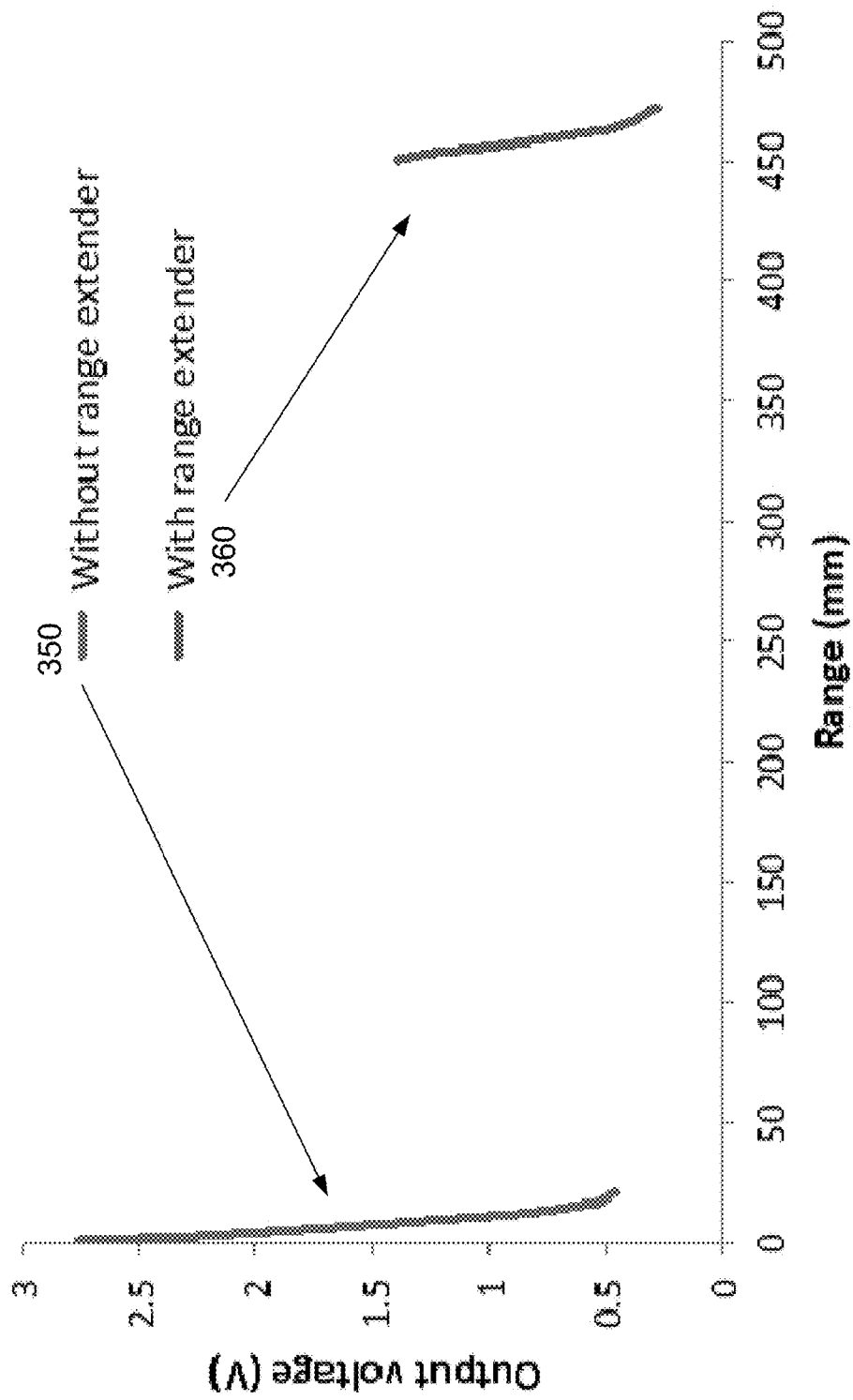
FIG. 8 is a graph showing an example of use of the WRAP system over varying distances with and without a range extender with paired coil.

FIG. 8 shows data collected from an embodiment with a range extender comprising two coils and a length of about 45 cm. The blue line 350 (on the left side) represents data from a setup that does not include a range extender and the red line 360 (on the right side) represents data obtain from a system that includes the range extender with a paired coil. In the absence of a range extender, the voltage drops below 0.5 V for the given input at a distance of about 15 mm. By contrast, incorporation of a range extender permits the output voltage to be maintained higher than 0.5 V for more than 450 mm (the entire length of the range extender under this embodiment). Thus, the range extender permits the power device (e.g. scanner) to be situated further away from the battery-less WRAP sensor (such as WRAP ECG sensor) and at a more convenient location on the subject's body. The range extender in this embodiment simply comprises two coils connected to each with a long wire pair. It can also include tuning capacitors, that can provide improved frequency selectivity.

The length of the range extender can be large, e.g., up to 500 cm. In embodiments, the range extender is up to about 100 cm in length. The range extender can be between about 10 and about 100 cm long. In one embodiment, the range extender is less than 50 cm in length. The length of the range extender can vary depending on the requirements of the user, such as the distance from the user's chest to the user's waist or pocket.

The systems and methods disclosed herein provide a cost-effective, more comfortable, and usable body-worn sensor network or system for unobtrusively collecting physiological and neurological body signals. The embodiments described herein may be used for various purposes including disease diagnosis and prognosis, physical activity monitoring, and early disease detection.

Thus, it should be understood that the embodiments and examples described herein have been chosen and described in order to best illustrate the principles of the invention and its practical applications to thereby enable one of ordinary skill in the art to best utilize the invention in various embodiments and with various modifications as are suited for particular uses contemplated. Even though specific embodiments of this invention have been described, they are not to be taken as exhaustive. There are several variations that will be apparent to those skilled in the art. Those skilled in the art will recognize, or be able to ascertain, using no more than routine experimentation, numerous equivalents to the specific substances and procedures described herein. Such equivalents are considered to be within the scope of this invention.

What is claimed is:

1. A wireless resistive analog passive sensor system, comprising:
    a scanner component comprising a scanning planar spiral coil;
    a sensor component comprising two identical planar spiral coils in conjugate orientation;
    wherein the system is configured to receive physiological signals where information is contained in differential inputs; and
    wherein each of said two conjugate planar spiral coils in the sensor component generate its own induced magnetic field, and the coils are situated in a mirror opposite configuration so that the induced magnetic fields generated by said two coils cancel each other when the received signals are common mode signals, but do not cancel each other when the received signals are differential mode signals.

2. The system of claim 1, wherein the physiological signals comprise EEG, EKG, ECG, or EMG signals.

3. The system of claim 1, wherein the system does not comprise a differential amplifier.

4. The system of claim 1, wherein the sensor component is battery-less.

5. The system of claim 1, further comprising a range extender.

6. The system of claim 5, wherein said range extender comprises a paired coil connecting the sensor component to the scanner component, said paired coil comprising a first coil and a second coil.

7. The system of claim 6, wherein the scanner component is physically separated from the sensor component.

8. The system of claim 6, wherein a first coil of the paired coil of the range extender is coaxially positioned adjacent to the coil in the scanner component, and the second coil of the paired coil of the range extender is positioned adjacent to the sensor component.

9. The system of claim 8, wherein the first coil and second coil of the range extender are connected by flexible wires.

10. The system of claim 9, further comprising one or more tuning capacitors connected in parallel to the first coil and second coil.

11. The system of claim 5, wherein said range extender comprises a plurality of paired coils connecting one or more sensor components to one or more scanner component.

* * * * *